(12) United States Patent
Magnusson et al.

(10) Patent No.: US 10,866,442 B2
(45) Date of Patent: Dec. 15, 2020

(54) CURVED, ARCUATELY-BONDED LIQUID CRYSTAL CELL AND METHOD OF MAKING

(71) Applicant: 3M INNOVATIVE PROPERTIES COMPANY, St. Paul, MN (US)

(72) Inventors: Kristina M. Magnusson, Djurmo (SE); Louise L. M. Madsen, Borlänge (SE); Larissa Zuravskaja, Borlänge (SE); Kenneth Jarefors, Falun (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/646,943

(22) PCT Filed: Aug. 27, 2018

(86) PCT No.: PCT/IB2018/056514
§ 371 (c)(1),
(2) Date: Mar. 12, 2020

(87) PCT Pub. No.: WO2019/053537
PCT Pub. Date: Mar. 21, 2019

(65) Prior Publication Data
US 2020/0278574 A1 Sep. 3, 2020

Related U.S. Application Data

(60) Provisional application No. 62/558,969, filed on Sep. 15, 2017.

(51) Int. Cl.
*G02F 1/1333* (2006.01)
*G02C 7/10* (2006.01)
(Continued)

(52) U.S. Cl.
CPC ........ *G02F 1/133305* (2013.01); *A61F 9/062* (2013.01); *G02C 7/101* (2013.01);
(Continued)

(58) Field of Classification Search
CPC ................................................. G02F 1/133305
See application file for complete search history.

(56) References Cited

U.S. PATENT DOCUMENTS

| 7,874,666 B2 | 1/2011 | Xu |
| 2006/0098153 A1 | 5/2006 | Slikkerveer |

(Continued)

FOREIGN PATENT DOCUMENTS

| JP | 2008-175914 | 7/2008 |
| WO | WO 1994-011779 | 5/1994 |

(Continued)

OTHER PUBLICATIONS

International Search Report for PCT International Application No. PCT/IB2018/056514, dated Dec. 14, 2018, 5 pages.

*Primary Examiner* — Alexander P Gross
(74) *Attorney, Agent, or Firm* — Kenneth B. Wood

(57) ABSTRACT

Curved, arcuately-bonded liquid-crystal cells that include substrates held together by an edge adhesive cured after the substrates were bent into a congruently curved configuration; methods of making such cells; and, switchable shutters and automatic darkening filters that include such cells.

22 Claims, 2 Drawing Sheets

(51) Int. Cl.
*G02F 1/1335* (2006.01)
*G02F 1/1337* (2006.01)
*G02F 1/1339* (2006.01)
*G02F 1/1341* (2006.01)
*G02F 1/1343* (2006.01)
*G02F 1/137* (2006.01)
*A61F 9/06* (2006.01)

(52) U.S. Cl.
CPC ............ *G02F 1/137* (2013.01); *G02F 1/1337* (2013.01); *G02F 1/1341* (2013.01); *G02F 1/13392* (2013.01); *G02F 1/13439* (2013.01); *G02F 1/133528* (2013.01); *G02F 2001/133354* (2013.01); *G02F 2001/133531* (2013.01); *G02F 2201/56* (2013.01); *G02F 2202/28* (2013.01)

(56) References Cited

U.S. PATENT DOCUMENTS

| | | |
|---|---|---|
| 2006/0203148 A1 | 9/2006 | Magnusson |
| 2009/0059126 A1 | 3/2009 | Koganezawa |
| 2010/0208190 A1* | 8/2010 | Yoshida ................ G02F 1/1341 349/160 |
| 2011/0255039 A1 | 10/2011 | Enomoto |
| 2011/0299025 A1 | 12/2011 | Sahouani |
| 2012/0292488 A1 | 11/2012 | Saadat |
| 2014/0013479 A1 | 1/2014 | Magnusson |
| 2014/0134406 A1* | 5/2014 | Son .......................... B32B 7/14 428/192 |
| 2014/0168546 A1* | 6/2014 | Magnusson ........... G02F 1/1333 349/14 |
| 2016/0262467 A1 | 9/2016 | Magnusson |
| 2016/0347045 A1 | 12/2016 | Sun |

FOREIGN PATENT DOCUMENTS

| | | |
|---|---|---|
| WO | WO 2016-044360 | 3/2016 |
| WO | WO 2016-126587 | 8/2016 |
| WO | WO 2017-192421 | 11/2017 |
| WO | WO 2018-229688 | 12/2018 |

* cited by examiner

US 10,866,442 B2

CURVED, ARCUATELY-BONDED LIQUID CRYSTAL CELL AND METHOD OF MAKING

CROSS REFERENCE TO RELATED APPLICATIONS

This application is a national stage filing under 35 U.S.C. 371 of PCT/IB2018/056514, filed Aug. 27, 2018, which claims the benefit of provisional Application No. 62/558,969, filed Sep. 15, 2017, the disclosure of which is incorporated by reference in its/their entirety herein.

BACKGROUND

Liquid-crystal cells have found use in widely varied applications in which the ability to control an amount of transmitted light is desired.

SUMMARY

In broad summary, herein are disclosed curved, arcuately-bonded liquid-crystal cells comprising substrates that are held together by an edge adhesive cured after the substrates were bent into a congruently curved configuration. Also disclosed are methods of making such curved, arcuately-bonded liquid-crystal cells. Also disclosed are switchable shutters, automatic darkening filters, and vision-protective headgear comprising such curved, arcuately-bonded liquid-crystal cells. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Terms such as "top", bottom", "upper", lower", "under", "over", "vertical", "horizontal", "front", "back", "forward", "rearward", and so on, will be understood to apply in their ordinary sense to a vision-protective headgear and to components thereof, as the headgear is worn by a human user standing upright. The term "inward" applies with reference to a liquid-crystal cell, components thereof (e.g. various layers as described herein) and various items used therewith (e.g. various polarization filters and so on), and denotes a direction toward the interior of the liquid-crystal cell. By way of specific example, a layer of liquid-crystal material is typically the inwardmost layer of a liquid-crystal cell. The term "outward" denotes a direction away from the interior of the liquid-crystal cell.

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−5% for quantifiable properties).

DETAILED DESCRIPTION

Disclosed herein are curved, arcuately-bonded liquid-crystal cells, methods of making such cells, and switchable shutters, automatic darkening filters, and vision-protective headgear that comprise at least one such curved, arcuately-bonded liquid-crystal cell.

Figure 1:
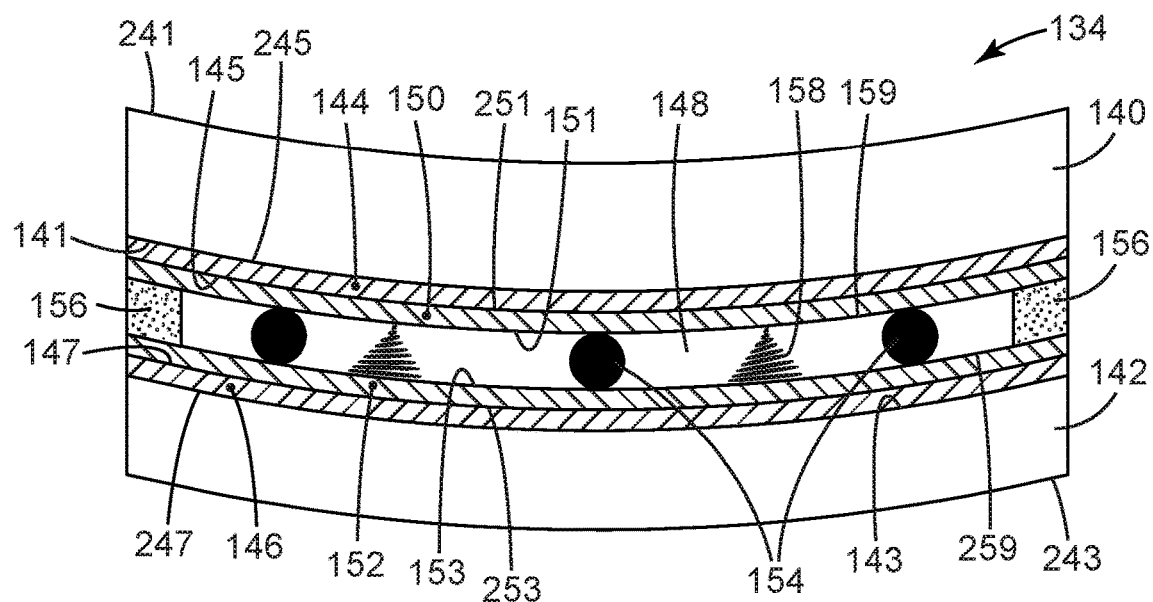
FIG. 1 is a schematic cross-sectional view of an exemplary curved, arcuately-bonded liquid-crystal cell.

FIG. 1 depicts a portion of an exemplary liquid-crystal cell 134 in side schematic cross-sectional view. Cell 134 is a laminar construction comprising two optically-transparent, flexible, multilayer glass-based substrates with a gap 148 therebetween. By "glass-based" is meant that the multilayer substrate must include at least one base layer that is a flexible glass sheet, e.g. sheets 140 and 142 as shown in FIG. 1. In various embodiments, the thickness of each glass sheet may be about 10 micrometers (µm) to 200 µm, more typically about 30 to 150 µm, and still more typically about 75 to 125 µm. In at least some embodiments, the glass sheets of the assembled, operational liquid-crystal cell are of identical thickness to the glass sheets as input into the cell-assembly process. In other words, such glass sheets are not e.g. etched, ablated, ground, or otherwise treated to reduce the thickness of the glass sheets after being bonded together. Each glass sheet is optically-transparent and thus may exhibit an optical transmission greater than greater than 80, 85, 90, 95, or 98% in the wavelength range of 380 nanometers (nm) to 750 nm. Such a glass sheet may be of any suitable composition, e.g. silica glass, borosilicate glass, and so on. In some embodiments, such a glass sheet may be a non-alkali glass, meaning that it has an alkali metal oxide level of 1000 parts per million (ppm) or less (preferably, of 500 ppm or less, and more preferably, of 300 ppm or less). In some embodiments, such a glass sheet may have one or more layers (e.g. protective layers, tie layers, and so on) disposed one or both major surfaces thereof, as long as such a layer or layers does not interfere with the ability of the glass sheet to be curved as disclosed herein and does not interfere with the optical transparency of the glass sheet. One example of a commercially-available flexible glass sheet is the product available from Schott AG (Mainz, Germany) under the trade designation D263T.

Each multilayer glass-based substrate further comprises a transparent conductive (electrode) layer that is disposed inwardly of the glass sheet (base layer) of the multilayer substrate. Thus as shown in FIG. 1, conductive layers 144 and 146 are respectively disposed inwardly of glass sheets 140 and 142. In specific embodiments, outward major surfaces 245 and 247 of conductive layers 144 and 146 are in contact with (e.g. are bonded to) inward major surfaces 141 and 143 of glass sheets 140 and 142. Such a transparent conductive layer may be made of any suitable material, e.g. indium tin oxide, that has been deposited or otherwise provided upon the inward major surface of the flexible glass sheet. Conductive layers 144 and 146 allow an electric field to be established across gap 148 between the substrates for purposes described later herein.

Each multilayer glass-based substrate further comprises a transparent alignment layer that is disposed inwardly of the transparent conductive layer of the multilayer substrate. Thus as shown in FIG. 1, alignment layers 150 and 152 are respectively disposed inwardly of transparent conductive layers 144 and 146. In specific embodiments, outward major surfaces 251 and 253 of alignment layers 150 and 152 are in contact with (e.g. are bonded to) inward major surfaces 145 and 147 of conductive layers 144 and 146. Such an alignment layer may be comprised e.g. of polyimide that has been deposited or otherwise provided upon the inward major surface of the conductive layer. The inward major surfaces (e.g. surfaces 151 and 153) of the alignment layers may be treated mechanically, such as by brushing or rubbing (or may be treated in any suitable manner), to impose a specific, predetermined alignment direction.

The alignment direction of major surface 151 and the alignment direction of major surface 153 will be chosen to have a predetermined, desired relationship (that is, to have a particular angle, e.g. an offset angle, therebetween). This will provide that upon disposing a nematic liquid-crystal material in a gap 148 between these two surfaces, the nematic molecules adjacent one surface will be oriented at a desired angle relative to the nematic molecules adjacent the other surface, in the absence of an electric field. In some embodiments, major surfaces 151 and 153 may be configured to have alignment directions that are substantially or essentially orthogonal (90 degrees) to each other. However, any suitable alignment angle may be used. For example, in some embodiments a low-twist angle may be used, e.g. with an alignment angle of e.g. 80, 70, 60 or 50 degrees. Low-twist arrangements are described in detail in US Patent Application Publication 20060203148 to Magnusson, which is incorporated by reference in its entirety herein. In some embodiments, a lower alignment angle (even as low as approximately 0 degrees) may be used.

A liquid-crystal cell as disclosed herein may thus comprise a first optically-transparent, flexible, multilayer glass-based substrate comprising (listed from outward to inward) a flexible glass sheet (base layer), a conductive layer, and an alignment layer. The liquid-crystal cell may comprise a second, similar substrate, with a gap 148 being present between the inwardmost major surfaces of the two substrates (these inwardmost major surfaces will typically be the inward major surfaces 151 and 153 of the alignment layers). The gap distance (i.e. the distance between inward major surfaces 151 and 153 of the alignment layers) may be any suitable value (often, in the range of 3-5 μm), and may be established and maintained by including spacers 154 within gap 148 as shown in FIG. 1.

The edges of the liquid-crystal cell can be sealed, and the overall assembly may be held together, by the use of an edge adhesive 156, as discussed later herein in detail. By definition, an edge adhesive 156 is required to be present at least partially within gap 148 between the two multilayer glass-based substrates and to hold the substrates together from within the gap. As such, an edge adhesive will be distinguished from e.g. such adhesives, gaskets or sealants as might be applied solely around external edges or surfaces of the liquid-crystal cell (although any such ancillary gasket or sealant may be used if desired). In at least some embodiments, the edge adhesive will be a flowable adhesive (rather than e.g. a pressure-sensitive adhesive that is not flowable to any significant extent). In some embodiments, an edge adhesive may be a photocurable adhesive, e.g. Norland Optical Adhesive 68, available from Norland Products, Cranbury, N.J. Other suitable edge adhesives may be e.g. the product available from 3M Company, St. Paul, Minn., under the trade designation CA8 Instant Adhesive, or the product available from Delo Industrial Adhesive Company, Windash, Germany, under the trade designation Delo Katiobond 698.

A liquid-crystal material 158 is disposed within gap 148 in a layer so that major surfaces 159 and 259 of the layer of liquid-crystal material are respectively in contact with major inward surfaces 151 and 153 of alignment layers 150 and 152. The liquid-crystal material can be any suitable nematic material, chosen e.g. from materials that are well known in the art. As will be well understood by artisans in the field, the inward major surfaces 151 and 153 of alignment layers 150 and 152 will cause the nematic molecules of the first major outward surface 159 of the layer of liquid-crystal material to be aligned at a desired, predetermined angular orientation in relation to the nematic molecules of the second major outward surface 259 of the layer of liquid-crystal material. (For example, the nematic molecules at these two surfaces may exhibit a twist angle of e.g. approximately 90, 80, 70, 60, 50, or 0 degrees, as discussed above.)

Figure 3:
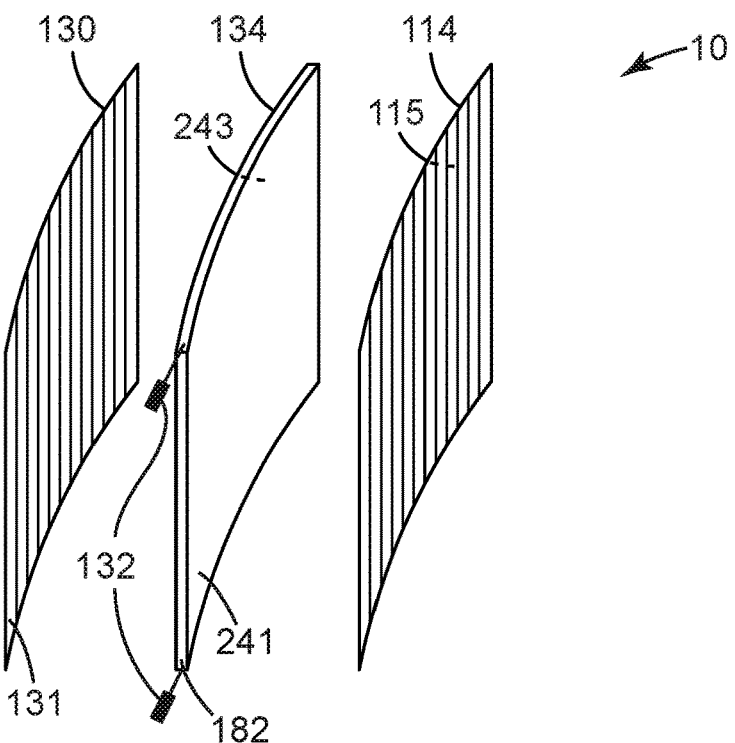
FIG. 3 is a side perspective view of an exemplary switchable shutter comprising a curved, arcuately-bonded liquid-crystal cell.

Liquid-crystal cell 134 may be provided with connectors 132 (as shown in FIG. 3) by which a control voltage can be applied to the cell. The application of a control voltage to conductive layers 144 and 146 will establish an electric field across gap 148 which will alter the arrangement of the nematic molecules. That is, the nematic liquid-crystal molecules will at least generally align with the electric field thus modifying the ability of the liquid-crystal molecules to affect the polarization state of the light passing through the liquid-crystal material. This, in combination with the presence of polarization filters as discussed later herein, can allow control of the amount of light that passes through a switchable shutter that includes the liquid-crystal cell.

By definition, liquid-crystal cell 134 and the various layers thereof (including glass sheets 140 and 142) is curved so as to exhibit a radius of curvature of less than 30 cm (e.g. when viewed along a vertical axis of a vision-protective headgear in which the liquid-crystal cell is installed), at least at one location of the liquid-crystal cell. In various embodiments, such a radius of curvature may be less than 25, 20, 15, or 10 cm. In further embodiments, the radius of curvature may be at least about 5 or 7 cm. In some embodiments the radius of curvature may be constant along the length of the liquid-crystal cell. In other embodiments the radius of curvature may vary; e.g. it may decrease toward each lateral (side) end of the cell. Thus, for example, a curved automatic darkening filter 60 that includes one or more curved switchable shutters comprising one or more such curved liquid-crystal cells, may comprise an arcuate front-central area (directly in front of the user's eyes) with a relatively small radius of curvature and may comprise right and left side areas that are less sharply curved (e.g. are relatively planer). Various configurations of such curved automatic darkening filters and of vision-protective headgear comprising such filters are discussed in detail later herein.

Congruently Curved

By definition, the glass sheets 140 and 142 of liquid-crystal cell 134 (as well as any transparent conductive layers and alignment layers) are congruently curved relative to each other. By this is meant that at every location along the length and breadth of the optically-active area (the area that comprises liquid-crystal material 158) of the liquid-crystal cell, the glass sheets 140 and 142 are locally parallel to each other. Specifically, at all such locations the respective inward surfaces 141 and 143 of the glass sheets will be locally parallel to each other so that the normal axes of the surfaces are aligned with each other to within plus or minus 5 degrees.

Arcuately Bonded

Liquid-crystal cell 134 is an arcuately-bonded cell. By this is meant that the first and second multilayer glass-based substrates (each comprising a glass sheet bearing a conductive layer and an alignment layer) are simultaneously bent (i.e., curved) out of a flat configuration into a congruently curved configuration (i.e. with a desired, predetermined radius of curvature) before the first and second substrates are bonded together. By this is specifically meant that the first and second substrates are brought together with an edge adhesive disposed therebetween and the substrates are simultaneously bent into their desired congruently curved configuration; then (while the substrates are maintained in this curved configuration) the edge adhesive is cured so as to permanently bond the substrates together.

It will be appreciated based on the disclosures herein that a curved, arcuately-bonded liquid-crystal cell can have significant advantages over, for example, a curved, "flat-bonded" cell formed by bonding multilayer glass-based substrates to each other and then bending the bonded substrates into a curved configuration. That is, a liquid-crystal cell comprising two glass sheets (and various other layers as noted) held together by an adhesive therebetween falls into the general category of so-called sandwich composites comprising two outer layers and an inner layer that bonds the two outer layers together. If the layers are bonded together while they are flat, any subsequent attempt to bend the bonded assembly into an arcuate shape causes one of the outer layers to be put into tension and the other to be put into compression, with shear forces being present in the bonding layer therebetween. This causes the bonded assembly to resist the applied bending force, which can be highly advantageous in the case of e.g. manufacturing flat panels that exhibit high resistance to bending (e.g. for structural components for vehicular or architectural applications). However, such a phenomenon can be disadvantageous in the case of assembling a liquid-crystal cell in a flat state and then bending it into an arcuate shape in which it is to remain. That is, a flat-bonded liquid-crystal cell, when bent into an arcuate shape, will exhibit elevated levels of internal stress which will render the cell more easily damaged (which may e.g. result in one or both of the glass sheets breaking and/or delaminating from the inner adhesive if the cell is dropped or roughly handled).

An arcuately-bonded liquid-crystal cell as disclosed herein will be subject to the usual forces that will develop individually in each glass sheet upon being bent; however, an arcuately-bonded cell will develop the above-described tensile/compressive/shear forces to a lesser degree since the glass sheets are not yet bonded together at the time that they are bent into the arcuate shape. Thus, a curved, arcuately-bonded liquid-crystal cell as described herein may exhibit advantageously superior resistant to breakage, delamination, and so on.

It will be appreciated that above-recited advantages are particularly applicable to liquid-crystal cells that rely on substrates that include a layer of glass as disclosed herein. That is, even though glass sheets are now available that exhibit sufficient flexibility to be bent into an arcuate configuration, they are still far stiffer than e.g. many plastic substrates, and thus are more susceptible to the above-described differential tensile/compressive/shear forces. Glass-based substrates thus benefit greatly from use of the arrangements disclosed herein.

A curved, arcuately-bonded liquid-crystal cell may be produced according to the following exemplary method. In these and other descriptions herein, reference will be made to "inward" and "outward" items (e.g., surfaces of various layers). As noted earlier herein, the term "inward" denotes a direction toward the interior of the liquid-crystal cell and the term "outward" denotes a direction away from the interior of the liquid-crystal cell. Such terminology will be used for convenience herein even as applied to the various items before they have been actually assembled into a liquid-crystal cell.

Figure 2:
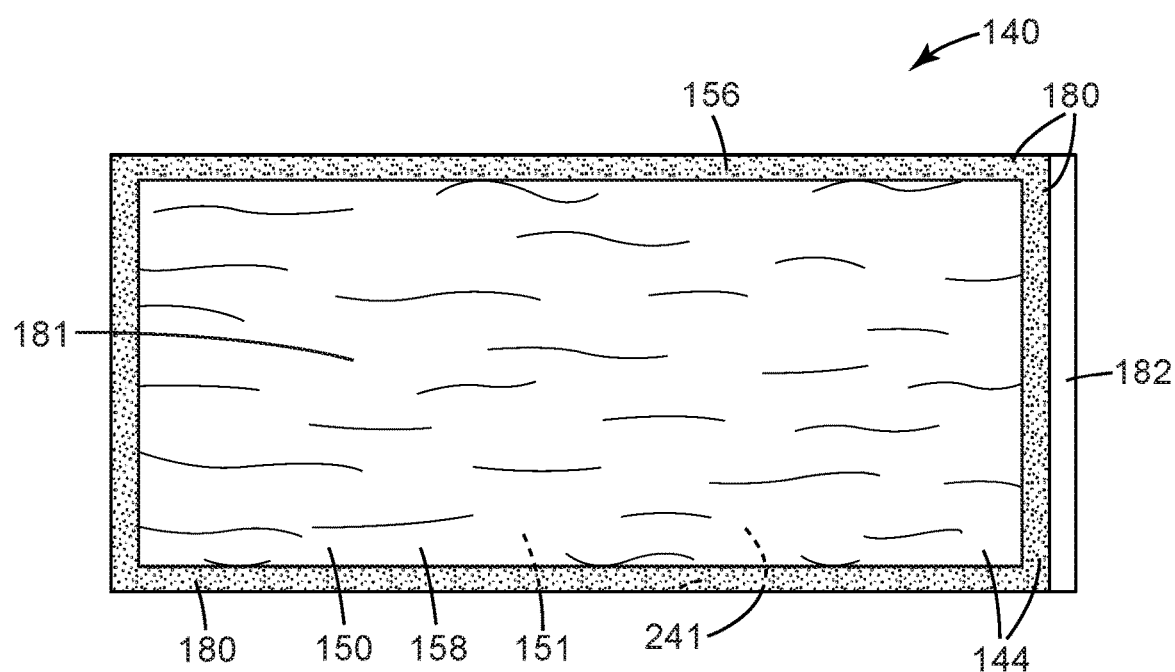
FIG. 2 is a plan view of an exemplary flexible, multilayer glass-based substrate with an edge adhesive, and a liquid-crystal material, disposed on an inwardmost major surface of the substrate.

To form a liquid-crystal cell as disclosed herein, a flexible, optically-transparent glass sheet 140 may be obtained as shown in exemplary embodiment in FIG. 2. In many convenient embodiments, the sheet may be elongated in one dimension, so that the sheet may be bent about a bending axis that is orthogonal to that long dimension. In specific embodiments, the sheet may be at least generally rectangular. Such a sheet may have a transparent conductive layer 144 deposited on at least the majority (i.e. greater than 50%) of the area of an inward major surface 141 of the sheet. In some embodiments, the transparent conductive layer may be deposited uniformly over the entirety of the inward major surface of the sheet; in other embodiments the transparent conductive layer may be deposited in a pattern e.g. if it is desired to provide multiple pixels in the resulting liquid-crystal cell. An alignment layer 150 may then be deposited on at least the majority of the inward major surface of the transparent conductive layer 144. In some embodiments, substantially all of the inward major surface of transparent conductive layer 144 may be covered by the alignment layer 150 except for e.g. an end region 182 along an edge of the substrate, which region comprises an exposed inward surface of conductive layer 144 so that an electrical connection can be established thereto (e.g. by a connector 132 as shown in FIG. 3).

As shown in exemplary embodiment in FIG. 2, a liquid-crystal material 158 may be deposited by any suitable coating or printing method onto at least a majority of the inward major surface 151 of the alignment layer 150 of the flexible multilayer glass-based substrate. The liquid-crystal material may be deposited e.g. as a continuous coating or it may be printed as droplets, as long as the droplets subsequently coalesce to form an at least substantially void-free liquid-crystal material. The liquid-crystal material 158 will occupy an interior region 181 of the inwardmost major surface (e.g. major surface 151 of the alignment layer) of the substrate, which region occupies at least a majority of this inwardmost major surface and may occupy as much as e.g. 60, 70, 90, 90 or 95% of this area. In many embodiments the liquid crystal material may be deposited onto the entirety of the inwardmost major surface except for a perimeter region 180 (e.g. a picture-frame border that circumferentially bounds interior region 181) which is reserved for an edge adhesive. Such a border may extend e.g. 2, 4, 6, 8 or 10 mm inward from each terminal edge (e.g., left, right, upper and lower edges) of the substrate.

An edge adhesive 156 is deposited along the entirety of the picture-frame border 180 as shown in exemplary embodiment in FIG. 2. The edge adhesive may be deposited before or after the liquid-crystal material is deposited, as desired. In some embodiments the edge adhesive may be deposited as a continuous bead; in other embodiments the edge adhesive may be deposited as droplets, as long as the droplets are able to coalesce with each other to provide a hermetic seal for the assembled liquid-crystal cell. (Coalescence of the adhesive and/or of the liquid-crystal material may occur e.g. spontaneously after the droplets are deposited; or, it may occur due to the forces that develop as the two substrates are pressed together in performing the assembly and bonding.)

Adhesive droplets may be deposited in a single row, or may be deposited in multiple rows or in a regular or irregular pattern. The edge adhesive may be provided so that upon the substrates being brought together, the edge adhesive in its final form is a strip that exhibits a width (in a direction perpendicular to the inward-outward axis of the liquid-crystal cell) of at least about 1, 2, 3, or 4 mm. In some embodiments, the edge adhesive and the liquid-crystal material may be deposited so that after final assembly of the liquid-crystal cell, there is little or no empty space left between the adhesive strip and the terminal edges of the liquid-crystal material. (In other words, the amount of liquid-crystal material that is deposited may be calculated so that it occupies at least substantially all of the region that is bounded by the edge adhesive.)

A first flexible, multilayer glass-based substrate bearing a liquid-crystal material 158 and an uncured edge adhesive 156 as described above, and as shown in exemplary embodiment in FIG. 2, may be brought into proximity with a second flexible, multilayer glass-based substrate that includes a transparent conductive layer and an alignment layer similar to those described above. In some embodiments the second substrate may have a size and shape that is similar to, or identical with, the first substrate. In some embodiments, spacers 154 (e.g. ceramic, glass, or polymeric spheres of uniform diameter) may be disposed on one or both of the substrates for the purposes discussed earlier herein. In various embodiments, this may be done e.g. by depositing the spacers onto the major surface of the alignment layer of the second substrate, or by depositing the spacers onto at least the layer of liquid-crystal material on the first substrate. In either case, upon bringing the substrates together as described below, the spacers will sink into the liquid-crystal material so that they establish a desired gap 148.

In some embodiments, the edge adhesive may be disposed so that upon bringing the two multilayer glass-based substrates together, the edge adhesive occupies substantially all of perimeter region 180 between the outer edges of the region 181 occupied by the liquid-crystal material, and the terminal edges of the first and second substrates (excepting e.g. an end region 182 as described elsewhere herein), as shown in exemplary embodiment in FIG. 2. In particular embodiments, the edge adhesive may be a flowable adhesive that spreads at least slightly under the slight pressure of the substrates being pressed brought together, to facilitate such a result. (It will thus be appreciated that in some embodiments the arrangement of an edge adhesive 156 as shown in FIG. 2 may not be achieved until the substrates are brought together.)

Disposing the edge adhesive in this manner may minimize the chance of exposed, oppositely-facing conductive surfaces of the multilayer glass-based substrates coming into close proximity or contact with each other in perimeter region 180. This may reduce any possibility of undesirable electrical pathways (e.g. short circuits) being established in perimeter region 180. In some embodiments, spacers 154 may be included in edge adhesive 156 to further ensure that the oppositely-facing conductive surfaces of the multilayer glass-based substrates do not approach each other too closely in perimeter region 180. Such spacers may be e.g. physically mixed into edge adhesive 156 before the adhesive is deposited on a substrate, or may be deposited onto a perimeter region 180 of an opposing substrate so that the spacers sink into the edge adhesive when the substrates are brought together.

The substrates may be brought together in any suitable manner. In some embodiments, both substrates may be put into an evacuable chamber (i.e., a vacuum chamber connected to a pump by which gaseous substances may be removed from the chamber). The first substrate, e.g. bearing the liquid-crystal material and the edge adhesive on an inwardmost major surface thereof, may be brought against a first vacuum fixture (e.g. a platen bearing a plurality of orifices) so that an outwardmost major surface of the first substrate is held securely against the surface of the first vacuum fixture. The second substrate (e.g. bearing the spacers on an inwardmost major surface thereof) may be brought against a second vacuum fixture so that an outwardmost major surface of the second substrate is held securely against the surface of the second vacuum fixture.

With the first and second substrates held securely by the vacuum fixtures within the evacuable chamber, the evacuable chamber can be closed and evacuated. In some embodiments, both the first and second substrates will be held in an at least substantially flat configuration by the first and second vacuum fixtures. The first and second vacuum fixtures can then be moved toward each other (which terminology encompasses moving one, or both, of the vacuum fixtures) to bring the substrates together. This does not imply that any portion of one substrate must necessarily come into direct contact with any portion of the other substrate. Rather, the substrates will move toward each other so that the liquid-crystal material and the edge adhesive that are on the inwardmost major surface of the first substrate, will come into contact with the inwardmost major surface of the second substrate. The substrates may be held together in this manner for any desired time, e.g. to allow the liquid-crystal material and/or the edge adhesive to coalesce and/or spread as desired. After this, the evacuable chamber can be opened and the two substrates (which at this point are held together by the liquid/wetting forces of the edge adhesive and the liquid-crystal material, but are not yet bonded together, and thus will be termed a "pre-assembly") may be released from the vacuum fixtures and removed from the chamber.

The unbonded pre-assembly comprising the two substrates and the liquid-crystal material and the uncured edge adhesive may then be curved (bent) into a desired arcuate shape. In many embodiments this may be conveniently done by bringing the pre-assembly into contact with a curved surface of a mandrel and conforming the pre-assembly to the curved surface of the mandrel. This may be done e.g. manually or by the use of robotic manipulation. The pre-assembly may then be held in this position while the edge adhesive is cured, by which is meant that the adhesive is hardened so that it has cohesive strength and also that the adhesive establishes a bond to the inward surface of each multilayer substrate with which it is in contact.

From the above discussions it will be appreciated that in many embodiments at least a portion of the edge adhesive may bond to a surface of an alignment layer or of a transparent conductive layer rather than bonding directly to a surface of the flexible glass sheet. It will thus be understood that the terminology of an edge adhesive being cured so that two multilayer glass-based substrates are held together, does not require that the adhesive must necessarily be bond to, or even be in direct contact with, any particular layers of the substrates. Rather, such terminology encompasses e.g. bonding to the flexible glass sheet, to the transparent conductive layer, and/or to the alignment layer, any or all of which may be bonded by the edge adhesive depending on the particular pattern of transparent conductive material and alignment material that is used.

In consideration of the above issues, an edge adhesive may be chosen to be able to satisfactorily bond to the chosen alignment layer. Moreover, in cases in which the edge adhesive bonds at least in part to the alignment layer rather than directly to the glass sheet, care should be taken that the bond between the alignment layer and the conductive layer, and between the conductive layer and the glass sheet, are adequate. It has been found that, for example, many photocurable adhesives are able to bond well to polyimide alignment layers; furthermore, many polyimide alignment layers are able to bond well to indium-tin-oxide conductive layers and many indium-tin-oxide conductive layers are able to bond well to glass.

In some embodiments the edge adhesive may be photocurable and may be cured via one or more electromagnetic radiation (e.g. UV) sources located within or behind the mandrel. In such embodiments the mandrel may be optically transparent (e.g. made of glass or quartz) to permit such operations. If desired, an opaque mask may be provided (e.g. mounted, temporarily or permanently, on or within the mandrel) to block radiation from entering liquid-crystal-containing area 181 to ensure that the electromagnetic radiation does not have any deleterious effect on the liquid-crystal material. The irradiation may be carried out under any conditions and for any length of time that is suitable for curing the edge adhesive. The pre-assembly may be maintained on the mandrel for any desired additional time (e.g. to allow for post-curing of the edge adhesive).

After curing is complete, the thus-formed liquid-crystal cell may be removed from the mandrel for further processing as desired. Such processing may include e.g. attachment of electrical connections to the liquid-crystal cell, attachment of polarization filters to the liquid-crystal cell, assembling multiple liquid-crystal cells and polarization filters together, and so on.

It will be appreciated that many variations on the above-presented exemplary method are possible and are encompassed within the disclosures herein. For example, the edge adhesive may be disposed on a first multilayer substrate and the liquid-crystal material may be disposed on the second multilayer substrate (or vice versa) rather than being disposed on the same substrate. If desired the spacers may be deposited onto the liquid-crystal material rather than being deposited on the substrate that does not bear the liquid-crystal material. If desired, a photocurable edge adhesive may be cured by using a radiation source that is located behind the pre-assembly rather than irradiating the pre-assembly from a source that is located within or behind the mandrel (in such cases the mandrel might not need to be optically clear). If desired, the two substrates may be bent into their congruently curved shape while they are still within the evacuable chamber rather than being removed from the chamber for such an operation. In some embodiments, the edge adhesive may be of a type that is curable by some other mechanism (e.g., by the use of heat, by exposure to moisture, or simply by the passage of time) rather than being photo-curable. In some embodiments, the two substrates may be assembled so that at least one substrate comprises an end region (e.g., the above-described end region 182) that protrudes past a terminal end of the other substrate to facilitate electrical connection to an exposed surface of a conductive layer present on the protruding end. In some convenient embodiments, the two substrates may be slightly offset relative to each other so that each substrate comprises a protruding end bearing a conductive end region 182.

In at least some embodiments the edge adhesive will be chosen and applied so that, upon being cured, the adhesive is present as a continuous strip that extends around the entirety of the perimeter region (picture-frame border) 180 so as to circumferentially bound area 181 that contains liquid-crystal material 158. By a continuous strip is meant that the adhesive is free of any through-passages that might allow air leaks; in other words, such an adhesive strip provides a hermetic seal for area 181 that contains liquid-crystal material 158.

In some embodiments, two movable vacuum fixtures need not be used. Rather, one multilayer glass-based substrate may remain stationary (whether on a floor of an evacuable chamber, on a shelf or platform within the chamber, or on a non-moving vacuum fixture within the chamber), with the other substrate being manipulated and moved into contact with the unmoving substrate.

In some embodiments, rather than the two substrates being brought together while held flat (e.g. by vacuum fixtures), an alternative procedure may be used. For example, a first substrate may be held at least generally flat and a second substrate may be temporarily forced into a curved condition. A first end of the second, temporarily-curved substrate may be brought into close proximity to a corresponding first end of the first substrate (so that the edge adhesive and the liquid-crystal material are in contact with the inwardmost major surfaces of both substrates at that end of each substrate). The second substrate can then be allowed to uncurl (flatten) from the first end to the second end (e.g. in a procedure akin to lamination of a flexible substrate to a rigid substrate) so that a line of contact of the liquid-crystal material and the edge adhesive with both substrates advances from the first end to the second end of the substrates as the uncurling of the second substrate proceeds. The end result is that the second substrate returns to its flat condition, with the edge adhesive and the liquid-crystal material now being in contact with the inwardmost major surfaces of both substrates over the entirety of the desired contact area. The resulting pre-assembly can then be bent into a curved configuration and bonded as described above.

In many embodiments, substrates may be used that comprise a generally elongated, e.g. rectangular, shape e.g. as in FIG. 2. Such substrates may be used in the production of an elongated, curved automatic darkening filter 60 of the general type depicted in FIG. 4. In some embodiments, the substrates may e.g. have various corners that are rounded, e.g. to different radii of curvature, as desired. In specific embodiments, curved, arcuately-bonded liquid-crystal cells may be used to produce automatic darkening filters that are provided separately for each eye (e.g., in the form of goggles comprised curved automatically-darkening "lenses"). It will thus be appreciated that terms such as a "picture-frame border" are used for convenience of description and do not require that the substrates, or the final liquid-crystal cell, must be strictly rectangular in shape.

It will be appreciated based on the disclosures herein that an ordinary artisan having background knowledge of the assembly of liquid-crystal cells would be able to identify an arcuately-bonded liquid-crystal cell (and in particular, would be able to distinguish such a cell from e.g. a flat-bonded liquid-crystal cell) by one or more of any number of detectable features and characteristics. For example, the discussions earlier herein indicate that a curved, arcuately-bonded liquid-crystal cell may exhibit an lower tendency to unbend toward a flat configuration, in comparison to a flat-bonded liquid-crystal cell. Also, the edge adhesive of a cell that is bonded while flat and then bent into a curved configuration will be under higher shear stress when the cell is curved than when the cell is flattened out; for an arcuately-bonded cell the opposite will be true. Such effects may be ascertained e.g. by performing a photoelastic inspection (e.g., examining phenomena such as birefringence under polarized light) of the edge adhesive with the cell in a flat condition and in a curved condition.

Still further, evidence may be found that indicates that the pre-assembly was bent into a curved configuration before the edge adhesive was cured (hardened). For example, an uncured adhesive will present little resistance to liquid flow during the process of bending the two substrates. It would thus be expected that some of the adhesive strips of an arcuately-curved cell would exhibit sidewalls with a slight slope consistent with the sidewalls of the uncured adhesive bead having deformed slightly due to the differential shear imparted to the uncured adhesive bead during the bending process. (In the simplest instance, an adhesive strip of an arcuately-bonded cell would exhibit a cross-sectional shape resembling a rhomboid rather than resembling a rectangle.) Moreover, it would be expected that differences could be observed in the sidewalls and/or the cross-sectional shape of adhesive strips that are oriented parallel to the bending axis (e.g. the beads on the short sides of the substrate pictured in FIG. 2) in comparison to the shape of adhesive strips that are oriented orthogonally to the bending axis (e.g., the beads on the long sides of the substrate pictured in FIG. 2). In contrast, an edge adhesive bead that is cured/hardened with the substrates flat, with the substrates being bent into a curved configuration only after the curing process is completed, would not be expected to exhibit any such evidence of liquid flow of the adhesive during the process of bending the substrates.

It will be understood that in actuality the various adhesive strips, as resulting from any commercial production process, will exhibit some inherent variation in cross-sectional shape and aspect. However, an artisan familiar with the assembly of liquid-crystal cells would nonetheless expect to be able to detect features attesting to whether or not the edge adhesive was in a flowable state, or was already cured and solidified, at the time that the substrates were bent into an arcuate shape.

It will also be evident to ordinary artisans that a curved, arcuately-bonded liquid-crystal cell as disclosed herein will be distinguishable from a curved liquid-crystal cell produced by obtaining substrates in a curved configuration that is stable (e.g., substrates of flexible plastic, or glass molded or ablated into a curved shape, which exhibit little or no tendency to flatten out into a flat configuration), and then bonding the substrates together while they are in their stable, curved configuration.

In many embodiments, a curved, arcuately-bonded liquid-crystal cell 134 may serve as part of a curved switchable shutter 10 as shown in exemplary embodiment in FIG. 3. The exemplary switchable shutter 10 as depicted in FIG. 3 includes a first polarization filter 114, a curved, arcuately-bonded liquid-crystal cell 134, and a second polarization filter 130. The polarization filters will be congruently curved to match the curvature of cell 134. In some embodiments, an inward major surface 115 of first polarization filter 114 may be bonded to an outward major surface 241 of first flexible glass sheet 140, as indicated in FIGS. 1 and 3. Similarly, an inward major surface 131 of second polarization filter 130 may be bonded to an outward major surface 243 of second flexible glass sheet 142.

In some embodiments, first and second polarization filters 114 and 130 may have substantially orthogonal polarization directions, in which the polarization direction of the first polarization filter 114 is oriented at approximately 90° to the polarization direction of the second polarization filter 130 as shown in exemplary embodiment in FIG. 3. These orthogonal polarization directions can enable the thus-produced switchable shutter 10 to maintain a "light" (e.g. highly-light transmissive) state when no control voltage is applied to cell 134 and to switch to a "dark" state and to maintain the dark state when a control voltage is applied to cell 134 (that is, to be power-darkening).

In some embodiments a switchable shutter may comprise a second curved, arcuately-bonded liquid-crystal cell that is sandwiched between one of the above-described polarization filters and a third polarization filter. Such a second liquid-crystal cell may be e.g. similar in design and configuration to the above-described liquid-crystal cell, but may be sandwiched between two polarization filters that have a different relative orientation than the first and second polarization filters described above. For example, the polarization directions of the second and third polarization filters may be e.g. substantially aligned with each other rather than being substantially orthogonal to each other, so that they can provide a switchable shutter that is power-lightening.

Ordinary artisans will appreciate that switchable shutters may often include e.g. two or three liquid-crystal cells and associated polarization filters, arranged and oriented in any suitable manner. In some embodiments, polarization filters may be oriented to each other at various angles (which may not necessarily be either strictly orthogonal or strictly parallel) e.g. to improve the performance of the thus-produced shutter when dealing with light at a variety of impingement angles. In various embodiments, any suitable orientation of the polarization filters may be used, e.g. to facilitate low twist angle arrangements as discussed earlier herein. Various exemplary arrangements of switchable shutters are described e.g. in U.S. Patent Application Publication Nos. 2014/0013479 and 2016/0262467, and in U.S. Provisional Patent Application No. 62/520,010, all of which are incorporated by reference in their entirety herein.

In some embodiments, such a switchable shutter, in addition to including one or more switchable assemblies of liquid-crystal cells, polarization filters, and so on, may also include one or more passive components such as e.g. a band pass filter that attenuates infra-red (IR) and/or ultra-violet (UV) wavelength components from high-intensity incident light. In some embodiments such a passive filter may take the form of a sheet that may serve as a flexible front or rear cover sheet for shutter 10.

Figure 4:
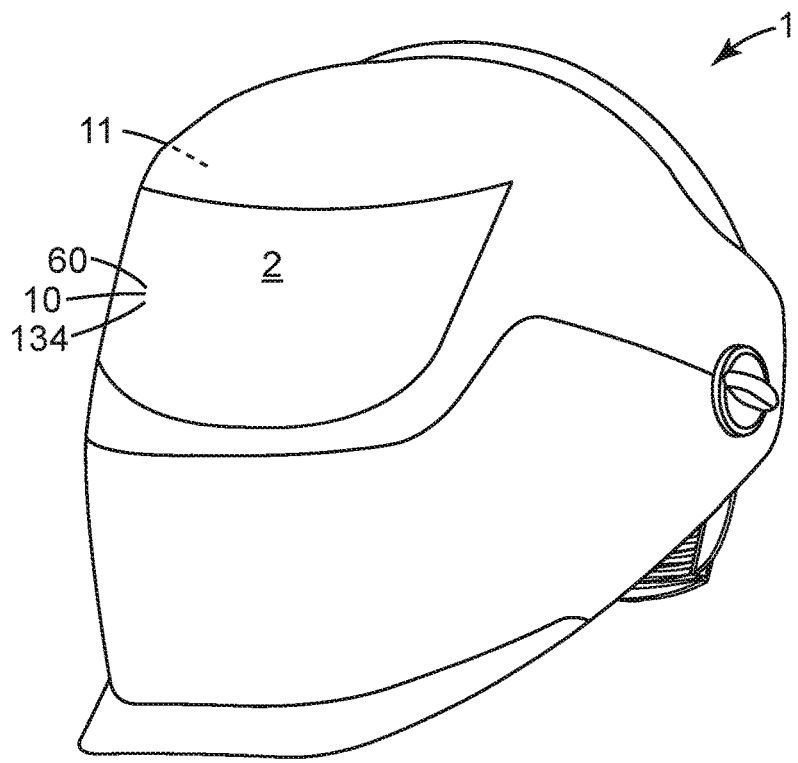
FIG. 4 is a front-side perspective view of an exemplary vision-protective headgear comprising a curved, arcuately-bonded liquid-crystal cell.

In many embodiments at least one switchable shutter 10 comprising at least one curved, arcuately-bonded liquid-crystal cell 134 may be mounted in a vision-protective headgear 1 and connected to a shutter control system 11 to provide a so-called automatic darkening filter 60 of the headgear, as shown in exemplary embodiment in FIG. 4. In many embodiments, the curved switchable shutter and the curved liquid-crystal cell thereof may be supported by a support frame for such purposes. Thus in at least some embodiments the liquid-crystal cell will not be provided e.g. with an ancillary film (e.g. a pre-tensioned film) that is adhesively bonded to the curved liquid-crystal cell and that applies tension to the cell for the purpose of imparting or maintain curvature of the cell. In some embodiments the automatic darkening filter may be provided as a module or cartridge that is installable, and removable, from the headgear. In other embodiments the automatic darkening filter may be permanently mounted in the headgear.

In various exemplary embodiments, protective headgear 1 may comprise e.g. a helmet, a shield, or a visor (e.g., a welding helmet, shield or visor), noting that there may not always be bright-line boundaries between protective headgear of these categories. As shown in exemplary embodiment in the front-side perspective view of FIG. 4, a protective headgear 1 may comprise a main body that (with headgear 1 as conventionally worn by a person) comprises a generally forward-facing portion that comprises an optically-transmissive window 2. In some embodiments, optically-transmissive window 2 may take the form of a through-opening; in other embodiments, it may have one or more transparent panes mounted therein. Automatic darkening filter 60 is mounted in headgear 1 so that filter 60 is aligned with at least a portion of window 2 so that filter 60 can filter electromagnetic radiation (e.g., visible light, ultraviolet radiation, infrared radiation, etc.) that passes through window 2. That is, automatic darkening filter 60 is positioned within protective headgear 1 so that any electromagnetic radiation that reaches the eyes of a person wearing the headgear must first pass through automatic darkening filter 60 to be optically filtered.

To provide an automatic darkening filter, the at least one switchable shutter 10 may be connected to any desired shutter control system 11. Such a shutter control system will be controllably connected to shutter 10 so that the shutter control system can at least send control signals to the shutter to cause the shutter to switch to and/or maintain any desired state of opacity (e.g., light, dark, intermediate, and so on). A shutter control system can switch a shutter between various states by the use of any convenient control signal; for example, by varying voltages that are applied to the shutter 10. In some embodiments protective headgear 1 may include at least one light sensor to which shutter control system 11 is connected. Such a light sensor may sense e.g. the light intensity that originates from a workview during ordinary use of headgear 1, and may send a signal that is representative of this light intensity, to shutter control system 11 by any suitable connection. In some embodiments, a shutter control system may include at least one image acquisition device as described in detail in U.S. (371) patent application Ser. No. 15/543,352.

Shutter control system 11 (and automatic darkening filter 60 and vision-protective headgear 1 in general) can comprise (in addition to any of the above-described components) various hardware, electronic, software and/or firmware components, integrated circuits, power sources, etc., as are needed to fully carry out the functioning of the shutter control system, and so on. Shutter control system is operatively connected to the switchable shutter and to other components as desired, by any suitable connections, which may be dedicated wires, optical fibers, wireless connections, etc. In some embodiments, protective headgear 1 may comprise a suspension, a portion of which is visible in FIG. 4 and which may be attached to protective headgear 1 by any suitable attachment mechanism. Regardless of the particular arrangements used, it will be understood that an automatic darkening filter as disclosed herein is distinguished from e.g. displays that include liquid-crystal cells. That is, an automatic darkening filter as disclosed herein operates to allow an actual workview, or an optically-filtered subset of that workview, to pass therethrough. This is distinguished from e.g. a display device that emits light on command, which emitted light does not originate from a workview.

At least the optically active portion (i.e., the portion that includes at least one liquid-crystal cell) of automatic darkening filter 60 is at least somewhat curved by way of including at least one curved, arcuately-bonded liquid-crystal cell 134. As noted previously herein, in many embodiments liquid-crystal cell(s) 134, and the resulting switchable shutter(s) 10 and automatic darkening filter 60, may be curved about a vertical axis. That is, such items will be curved along at least a portion of their lateral extent when in top view (i.e. when viewed from above the head of a person wearing the vision-protective headgear). In various embodiments, the automatic darkening filter may exhibit readily identifiable curvature (e.g. corresponding to a radius of curvature of less than about 20 cm) along at least 20, 40, 80, or essentially 100% of its lateral extent when viewed in top view. The physical properties of the optically-transparent, flexible, multilayer glass-based substrate and the methods of assembly disclosed herein may allow for curved automatic darkening filters to be manufactured which have a radius of curvature of e.g. about 5 cm to 30 cm, in combination with an optically active viewing area of about 10 to 600 square centimeters ($cm^2$), more typically 30 $cm^2$ to 250 $cm^2$.

Often, protective headgear 1 may be configured so that when the protective headgear is worn by a user, a laterally central area of automatic darkening filter 60 is positioned in front of the user's eyes. In some embodiments, automatic darkening filter 60 may comprise areas (that are integrally connected to, and extend from, the laterally central area) that wrap at least partially around toward the left and right lateral sides of the protective headgear to a desired extent. While a relatively small extent of side-wrap is present in the exemplary design of FIG. 4, any amount of side-wrap can be used as desired. The front/central area, and side areas, of the automatic darkening filter can differ in curvature if desired.

Protective headgear comprising an automatic darkening filter as described herein can be used in connection with industrial operations, for example welding (e.g. arc welding, torch welding, acetylene welding), cutting (e.g. laser cutting, acetylene cutting), brazing, soldering and the like. They also can be used in connection with medical procedures involving high intensity light (e.g. laser surgery, hair removal, tattoo removal, light-curing of dental resins, etc.) and other uses.

List of Exemplary Embodiments

Embodiment 1 is a curved, arcuately-bonded liquid-crystal cell comprising: first and second optically-transparent, flexible, multilayer glass-based substrates that are congruently curved and that define a gap between an inwardmost major surface of the first substrate and an inwardmost major surface of the second substrate, and, a curved layer of liquid-crystal material disposed in the gap between the first and second substrates and in contact with the inwardmost major surface of the first substrate and the inwardmost major surface of the second substrate; wherein the first and second substrates are held together by an edge adhesive disposed within the gap between the first and second substrates and cured after the first and second substrates were bent into their congruently curved configuration, so that the liquid-crystal cell is a curved, arcuately-bonded liquid-crystal cell.

Embodiment 2 is the curved, arcuately-bonded liquid-crystal cell of embodiment 1 wherein the first and second substrates each comprise a transparent conductive layer disposed on an at least a majority of an inward major surface of a flexible glass sheet of the substrate.

Embodiment 3 is the curved, arcuately-bonded liquid-crystal cell of embodiment 2 wherein the first and second substrates each comprise an alignment layer disposed on at least a majority of an inward major surface of the transparent conductive layer of the substrate, each of which alignment layers comprises an inward major surface that provides the inwardmost major surface of the substrate and that is in contact with a outward major surface of the liquid-crystal material.

Embodiment 4 is the curved, arcuately-bonded liquid-crystal cell of embodiment 3 wherein the edge adhesive is present as a continuous strip that extends along an entirety of a picture-frame border of the substrates and that completely circumferentially bounds an interior area of the gap that contains the liquid-crystal material.

Embodiment 5 is the curved, arcuately-bonded liquid-crystal cell of embodiment 4 wherein at least at some locations along the strip of edge adhesive, the edge adhesive is in contact with, and is bonded to, the inward major surface of the first alignment layer and the inward major surface of the second alignment layer.

Embodiment 6 is the curved, arcuately-bonded liquid-crystal cell of any of embodiments 3-5 wherein the edge adhesive is a coalesced adhesive that was deposited on an inwardmost major surface of the first substrate or of the second substrate, in the form of droplets that coalesced into a continuous bead to provide the continuous adhesive strip after curing of the adhesive.

Embodiment 7 is the curved, arcuately-bonded liquid-crystal cell of any of embodiments 1-6 wherein the curved, arcuately-bonded liquid-crystal cell comprises a multiplicity of discrete spacers randomly distributed throughout a length and breadth of the curved layer of liquid-crystal material.

Embodiment 8 is a curved switchable filter comprising: a curved first polarization filter having a first polarization direction; a curved second polarization filter having a second polarization direction, which may be the same or different from the first polarization direction; and, a curved, arcuately-bonded liquid-crystal cell of any of embodiments 1-7 sandwiched between the first and second polarization filters, wherein the curved switchable filter is capable of being switched between at least a dark state and a light state.

Embodiment 9 is the curved automatic darkening filter comprising: at least one curved switchable shutter of embodiment 8, and a shutter control system that is controllably connected to the switchable shutter.

Embodiment 10 is a vision-protective headgear comprising: a curved automatic darkening filter of embodiment 9 mounted in an optically transmissive window of the vision-protective headgear.

Embodiment 11 is a method of making a curved, arcuately-bonded liquid-crystal cell, the method comprising: depositing an edge adhesive along a picture-frame border of an inwardmost major surface of a first optically-transparent, flexible, multilayer glass-based substrate; depositing a liquid-crystal material onto an interior area of the inwardmost major surface of the first optically-transparent, flexible, multilayer glass-based substrate or onto an interior area of an inwardmost major surface of a second optically-transparent, flexible, multilayer glass-based substrate; then, bringing the first and second substrates together so that the edge adhesive is in contact with the inwardmost major surface of the first substrate and with the inwardmost major surface of the second substrate; then, simultaneously bending the first substrate and the second substrate into a congruently curved configuration; then, curing the edge adhesive while the first substrate and the second substrate are held in the congruently curved configuration, to produce a curved, arcuately-bonded liquid-crystal cell.

Embodiment 12 is the method of embodiment 11 wherein the first substrate and the second substrate are held in the congruently curved configuration by a temporary holding fixture, and wherein after the edge adhesive is cured the curved, arcuately-bonded liquid-crystal cell is released from the temporary holding fixture.

Embodiment 13 is the method of any of embodiments 11-12 wherein after the first and second substrates are brought together the interior area containing the liquid-crystal material is completely circumferentially bounded by the edge adhesive.

Embodiment 14 is the method of any of embodiments 11-13 wherein the edge adhesive is deposited along the picture-frame border of the inwardmost major surface of the first substrate in the form of droplets, which droplets, after being deposited on the major surface, coalesce with each other to form a continuous bead that provides a continuous adhesive strip after curing the adhesive.

Embodiment 15 is the method of any of embodiments 11-14 wherein the edge adhesive is a photo-curable adhesive.

Embodiment 16 is the method of any of embodiments 11-15 wherein the first and second substrates are simultaneously bent into the congruently curved configuration by being urged against a curved surface of a mandrel.

Embodiment 17 is the method of embodiment 16 wherein the edge adhesive is a photo-curable adhesive and wherein a source of electromagnetic radiation that is positioned on an opposite side of the mandrel from the curved surface against which the first and second substrates are urged, is activated to photo-cure the edge adhesive through a transparent portion of the mandrel.

Embodiment 18 is the method of embodiment 17 wherein a predetermined area of the mandrel is optically masked so that electromagnetic radiation does not pass therethrough, and wherein the first and second substrates are positioned relative to the optically masked area of the mandrel so that the liquid-crystal material is shaded from the source of electromagnetic radiation.

Embodiment 19 is the method of any of embodiments 11-18 wherein: the depositing of the edge adhesive onto the inwardmost major surface of the first substrate is done with the first substrate held in a flat configuration; and, the depositing of the liquid-crystal material onto the inwardmost major surface of the first substrate or of the second substrate is done with the substrate on which the liquid-crystal material is deposited held in a flat configuration.

Embodiment 20 is the method of any of embodiments 11-19 wherein the bringing of the first and second substrates together so that the edge adhesive is in contact with the inwardmost major surface of the first substrate and with the inwardmost major surface of the second substrate, is done by the following steps: placing the first and second substrates into an evacuable chamber; holding the first substrate in a flat configuration by a first vacuum fixture within the evacuable chamber; holding the second substrate in a flat configuration by a second vacuum fixture within the evacuable chamber; closing the evacuable chamber and evacuating the gaseous contents of the evacuable chamber; then, while the evacuable chamber is maintained in an evacuated condition and while the first and second substrates are each held in a flat configuration, bringing the first and second vacuum fixtures toward each other to bring the first and second substrates together so that the edge adhesive is in contact with the inwardmost major surface of the first substrate and with the inwardmost major surface of the second substrate.

Embodiment 21 is the method of embodiment 11 wherein the bringing of the first and second substrates together so that the edge adhesive is in contact with the inwardmost major surface of the first substrate and with the inwardmost major surface of the second substrate, is done by the following steps: holding one of the substrates in a flat condition; temporarily forcing the other substrate into a curved condition; bringing a first-end region of the temporarily-curved substrate into proximity with a first-end region of the flat substrate, then allowing the temporarily-curved substrate to flatten from its temporarily-curved condition back towards a flat condition, the flattening process proceeding from the first end of the temporarily-curved substrate to a second end of the temporarily-curved substrate, so that a remaining region of the temporarily-curved substrate comes into proximity with a remaining region of the flat substrate as the flattening process proceeds from the first end of the temporarily-curved substrate to the second end of the temporarily-curved substrate.

Embodiment 22 is the method of any of embodiments 11-21 wherein the method further comprises sandwiching the curved, arcuately-bonded liquid-crystal cell between a curved first polarization filter having a first polarization direction and a curved second polarization filter having a second polarization direction, which may be the same or different from the first polarization direction, to produce a curved switchable filter capable of being switched between at least a dark state and a light state.

Embodiment 23 is the method of embodiment 22 further comprising the step of connecting a shutter control system to the curved switchable filter to form an automatic darkening filter. Embodiment 24 is the method of embodiment 23 further comprising the step of installing the automatic darkening filter into a vision-protective headgear.

Example

A curved, arcuately-bonded liquid-crystal cell was made in the following manner.

Flexible glass sheets were obtained of the general type described in U.S. Published Patent Application No. 2014/0168546. Each glass sheet was approximately 0.1 mm thick and of rectangular shape with a size approximately 80×140 mm. Each glass sheet had a continuous, transparent conductive coating of ITO (indium tin oxide) on the entirety of one major surface of one side (which would become the "inward" side upon assembly of the liquid-crystal cell) of the glass sheet.

Two such glass sheets were each coated with a thin layer of commercially available polyimide alignment material. The polyimide alignment material was coated by ink-jetting, onto the "inward" (ITO-bearing side) of each sheet. The polyimide alignment material was coated onto the entirety of the ITO-bearing major surface, except for a small end region (extending inward from a short edge of the sheet, a distance of approximately 2 mm), thus leaving this end region with exposed ITO. The polyimide alignment material was cured on a hotplate at a temperature in the range of approximately 230° C., providing a continuous layer of polyimide alignment material. The exposed surface of the polyimide alignment material of each glass sheet was then aligned by a mechanical rubbing process, using a rotating felt cloth to brush the surface in a specified direction. The alignment material of the first glass sheet was aligned in a first direction and the alignment material of the second glass sheet was aligned in a second direction that was oriented approximately 80 degrees away from the first direction.

A commercially available, flowable, photocurable (UV curable) edge adhesive was applied to a first of the above-described glass sheets by a jetting process. The edge adhesive was applied to the inward (ITO/polyimide-bearing) side of the sheet, as an elongated bead located a desired distance slightly inward from the terminal edges of the glass sheet. Specifically, the bead was located approximately 1.5 mm inward from three of the edges of the glass sheet, and approximately 3.5 mm inward from the fourth edge (the edge comprising the end region with exposed ITO, to be used for attaching an electrical connector).

The interior area of the inward major surface of the sheet (i.e., the area that was circumferentially bounded by the bead of edge adhesive) was coated with liquid-crystal material by ink-jetting. The liquid-crystal material was a commercially available, nematic material.

This first glass sheet was positioned on a horizontal surface near the bottom of a vacuum chamber, with the inward side (the side bearing the edge adhesive and the liquid-crystal material) facing upward.

The inward (ITO/polyimide-bearing) side of the second glass sheet was sprayed with 4 μm diameter spacer beads using an air brush. The spacer beads were deposited over the entire surface of this second glass sheet, including the area that was to come in contact with the edge adhesive that was provided on the first glass sheet. The second glass sheet was positioned, inward side up, on a horizontal, upward-facing surface of a movable/rotatable vacuum fixture (a vacuum table) that was located above the first glass sheet in the vacuum chamber. A vacuum was applied to the vacuum table so that the second glass sheet was securely held by the vacuum table, after which the vacuum table was rotated so that the second glass sheet was inverted with the inward side of the second glass sheet facing down above the first glass sheet. (The spacer beads were adequately held to the inward surface of the second glass sheet by electrostatic forces.) The two glass sheets were positioned (displaced horizontally relative to each other) so that there was an approximately 2 mm offset between the terminal edges of the glass sheets, at each of the short edges of the sheets. Both of the glass sheets were held flat during these operations.

The vacuum chamber was closed and air was evacuated. While maintaining the vacuum, the vacuum table holding the second glass sheet was smoothly lowered until the two glass sheets approached each other and were slightly pressed together. The vacuum chamber was then ventilated and opened. The vacuum holding the second glass sheet to the vacuum table was released after which the vacuum table was moved upward, clear of the glass sheets.

The resulting flat "pre-assembly" of the two glass sheets and the various layers and materials thereupon, was removed from the chamber. The slight pressing together of the two glass sheets had resulted in the edge seal material (which beforehand had still exhibited at least some individual dots) coalescing and spreading to form a continuous stripe of adhesive with a width of approximately 2-3 mm, extending around the entire perimeter of each glass sheet (although leaving an above-mentioned end region of exposed ITO at one short end of each glass sheet). The rectangular, interior area bounded by the adhesive stripe contained an approximately 4 μm thick layer of liquid-crystal mixture. (The liquid-crystal material, being of lower viscosity than the edge adhesive, had mostly coalesced to form a continuous layer before the glass sheets were brought together; the slight pressing together of the glass sheets ensured that the liquid-crystal material was fully coalesced). The amount of liquid-crystal material had been calculated (based on the 4 µm width of the gap to be established by the spacer beads, in combination with the size of the interior area to be occupied by the liquid-crystal material) so that the liquid-crystal material substantially filled the entirety of this interior area closely up to the interior edges of the adhesive stripe.

The pre-assembly was then carefully manually bent onto the outer surface of a curved portion of a half-cylinder mandrel made of transparent quartz. A flexible compression band (which covered the entirety of the preassembly) was snugly fit over the pre-assembly to hold the preassembly in place on the curved surface of the mandrel. The edge adhesive was then cured by illuminating the adhesive with UV light emitted from LED sources positioned within the quartz half-cylinder. (No masking of the liquid-crystal material was needed with the LED sources used.) After the curing of the edge adhesive, the compression band was released and the thus-produced curved, arcuately-bonded liquid-crystal cell could be removed from the quartz half-cylinder.

As noted, the glass sheets had been offset (displaced horizontally) from each other so that each glass sheet comprised a protruding end along a short edge thereof, with an exposed end region bearing accessible, conductive ITO. Sheet connectors were attached to the ITO layer of each glass sheet (at opposite ends of the liquid-crystal cell) to establish electrical connections for operating the liquid-crystal cell.

Others layers, components, and so on, could then be added to the curved, arcuately-bonded liquid-crystal cell to form a switchable shutter. For example, polarizing filters could be bonded, e.g. with an optically-clear pressure-sensitive adhesive, to one or both of the exposed outward major surfaces of the glass sheets.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document incorporated by reference herein, this specification as written will control.

What is claimed is:

1. A method of making a curved, arcuately-bonded liquid-crystal cell, the method comprising:

depositing a photocurable edge adhesive along a picture-frame border of an inwardmost major surface of a first optically-transparent, flexible, multilayer glass-based substrate;

depositing a liquid-crystal material onto an interior area of the inwardmost major surface of the first optically-transparent, flexible, multilayer glass-based substrate or onto an interior area of an inwardmost major surface of a second optically-transparent, flexible, multilayer glass-based substrate; then, bringing the first and second substrates together so that the photocurable edge adhesive is in contact with the inwardmost major surface of the first substrate and with the inwardmost major surface of the second substrate; then, simultaneously bending the first substrate and the second substrate into a congruently curved configuration by urging them against a curved surface of a mandrel; then, while the first substrate and the second substrate are held in the congruently curved configuration, photocuring the photocurable adhesive by activating a source of electromagnetic radiation positioned on an opposite side of the mandrel from the curved surface against which the first and second substrates are urged, so as to photocure the photocurable edge adhesive through a transparent portion of the mandrel to produce a curved, arcuately-bonded liquid-crystal cell.

2. The method of claim 1 wherein the first substrate and the second substrate are held in the congruently curved configuration by a temporary holding fixture, and wherein after the edge adhesive is cured the curved, arcuately-bonded liquid-crystal cell is released from the temporary holding fixture.

3. The method of claim 1 wherein after the first and second substrates are brought together the interior area containing the liquid-crystal material is completely circumferentially bounded by the edge adhesive.

4. The method of claim 1 wherein the edge adhesive is deposited along the picture-frame border of the inwardmost major surface of the first substrate in the form of droplets, which droplets, after being deposited on the major surface, coalesce with each other to form a continuous bead that provides a continuous adhesive strip after curing the adhesive.

5. The method of claim 1 wherein a predetermined area of the mandrel is optically masked so that electromagnetic radiation does not pass therethrough, and wherein the first and second substrates are positioned relative to the optically masked area of the mandrel so that the liquid-crystal material is shaded from the source of electromagnetic radiation.

6. The method of claim 1 wherein:

the depositing of the edge adhesive onto the inwardmost major surface of the first substrate is done with the first substrate held in a flat configuration; and, the depositing of the liquid-crystal material onto the inwardmost major surface of the first substrate or of the second substrate is done with the substrate on which the liquid-crystal material is deposited held in a flat configuration.

7. The method of claim 1 wherein the bringing of the first and second substrates together so that the edge adhesive is in contact with the inwardmost major surface of the first substrate and with the inwardmost major surface of the second substrate, is done by the following steps:

placing the first and second substrates into an evacuable chamber;

holding the first substrate in a flat configuration by a first fixture within the evacuable chamber;

holding the second substrate in a flat configuration by a second fixture within the evacuable chamber;

closing the evacuable chamber and evacuating the gaseous contents of the evacuable chamber;

then, while the evacuable chamber is maintained in an evacuated condition and while the first and second substrates are each held in a flat configuration, bringing the first and second fixtures toward each other to bring the first and second substrates together so that the edge adhesive is in contact with the inwardmost major surface of the first substrate and with the inwardmost major surface of the second substrate.

8. The method of claim 1 wherein the photocurable adhesive is a flowable adhesive that is not a pressure-sensitive adhesive.

9. The method of claim 1 wherein the first and second substrates respectively include first and second flexible glass sheets of thickness 30-150 microns.

10. The method of claim 9 wherein the process of making the curved, arcuately-bonded liquid-crystal cell does not include a step of etching, ablating, grinding, or otherwise reducing the thickness of the first or second flexible glass sheets, so that the first and second flexible glass sheets of the curved, arcuately-bonded liquid-crystal cell are of identical thickness to the first and second flexible glass sheets as were input into the process of making the curved, arcuately-bonded liquid crystal cell.

11. The method of claim 1 wherein in the curved, arcuately-bonded liquid-crystal cell, at least one of the first and second substrates comprises an end region that protrudes past a terminal end of the other substrate, with an exposed surface of a conductive layer being present on the protruding end region.

12. The method of claim 11 wherein the first and second substrates are offset relative to each other so that each substrate comprises a protruding end region bearing an exposed surface of a conductive layer.

13. The method of claim 1 wherein the curved, arcuately-bonded liquid-crystal cell comprises a multiplicity of discrete spacers randomly distributed throughout a length and breadth of the liquid-crystal material.

14. The method of claim 13 wherein additional discrete spacers are present in the edge adhesive.

15. The method of claim 1 wherein the first and second substrates each comprise a transparent conductive layer disposed on at least a majority of an inward major surface of a flexible glass sheet of the substrate.

16. The method of claim 15 wherein the first and second substrates each comprise an alignment layer disposed on at least a majority of an inward major surface of the transparent conductive layer of the substrate, each of which alignment layers comprises an inward major surface that provides the inwardmost major surface of the substrate and that is in contact with an outward major surface of the liquid-crystal material.

17. The method of claim 16 wherein at least at some locations along the strip of edge adhesive, the edge adhesive is in contact with, and is bonded to, the inward major surface of the first alignment layer and the inward major surface of the second alignment layer.

18. The method of claim 1 wherein the method further comprises sandwiching the curved, arcuately-bonded liquid-crystal cell between a curved first polarization filter having a first polarization direction and a curved second polarization filter having a second polarization direction, which may be the same or different from the first polarization direction, to produce a curved switchable filter capable of being switched between at least a dark state and a light state.

19. The method of claim 18 further comprising the step of connecting a shutter control system to the curved switchable filter to form an automatic darkening filter.

20. The method of claim 19 further comprising the step of installing the automatic darkening filter into a vision-protective headgear.

21. The method of claim 20 wherein the vision-protective headgear is a helmet and wherein the automatic darkening filter is installed into a generally forward-facing, optically-transmissive window of the helmet.

22. The method of claim 21 wherein the helmet is a welding helmet.

* * * * *